(12) United States Patent
Mckinnon et al.

(10) Patent No.: US 12,714,832 B2
(45) Date of Patent: Aug. 25, 2026

(54) CENTRAL CATHETERS, ASSEMBLIES, AND METHODS THEREOF

(71) Applicant: Bard Access Systems, Inc., Salt Lake City, UT (US)

(72) Inventors: Austin J. Mckinnon, Herriman, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 688 days.

(21) Appl. No.: 18/110,300

(22) Filed: Feb. 15, 2023

(65) Prior Publication Data

US 2023/0256209 A1 Aug. 17, 2023

Related U.S. Application Data

(60) Provisional application No. 63/310,533, filed on Feb. 15, 2022.

(51) Int. Cl.
*A61M 25/06* (2006.01)
*A61M 25/00* (2006.01)

(52) U.S. Cl.
CPC ...... *A61M 25/065* (2013.01); *A61M 25/0026* (2013.01)

(58) Field of Classification Search
CPC ........ A61M 25/0097; A61M 25/09041; A61M 25/065; A61M 25/0026; A61M 25/0075;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 102018102390 A1 8/2019
EP 0730880 A1 9/1996
(Continued)

OTHER PUBLICATIONS

PCT/US2020/056364 filed Oct. 19, 2020 International Preliminary Report on Patentability dated Apr. 19, 2022.
(Continued)

*Primary Examiner* — Kevin C Sirmons
*Assistant Examiner* — Alexandra Lalonde
(74) *Attorney, Agent, or Firm* — Rutan & Tucker LLP

(57) ABSTRACT

Central catheters, central catheter assemblies, and methods thereof. A central catheter includes a catheter tube coupled with a number of extension legs, a needle hub coupled with the catheter tube, where the needle hub is configured to receive a needle therethrough so that the needle is disposed within a primary catheter tube lumen. The central catheter includes a manifold hub for coupling the number of extension legs with the catheter tube. The manifold hub may be integral to the needle hub. The needle hub includes a septum within a needle-hub lumen, where the septum is configured to define a fluid tight seal with the needle and to prevent fluid flow through a proximal portion of the needle-hub lumen when the needle is withdrawn from the needle-hub lumen. A method for introducing a central catheter into a blood vessel.

20 Claims, 9 Drawing Sheets

(58) Field of Classification Search
CPC .. A61M 25/06; A61M 25/0606; A61M 25/01; A61M 25/09; A61M 25/0023; A61M 25/002; A61M 39/0693; A61M 2039/2433; A61M 2039/0036; A61M 2039/064; A61M 2039/0666; A61M 2025/0034; A61M 2025/0036; A61M 2025/0037; A61M 2025/0039; A61M 2025/0062; A61M 2025/0076; A61B 2017/3445
See application file for complete search history.

(56) References Cited

U.S. PATENT DOCUMENTS 3,890,976 A 6/1975 Bazell et al.
4,205,675 A 6/1980 Vaillancourt
4,292,970 A 10/1981 Hession, Jr.
4,468,224 A 8/1984 Enzmann et al.
4,525,157 A 6/1985 Vaillancourt
4,581,019 A 4/1986 Curelaru et al.
5,017,259 A 5/1991 Kohsai
5,040,548 A 8/1991 Yock
5,057,073 A 10/1991 Martin
5,112,312 A 5/1992 Luther
5,120,317 A 6/1992 Luther
5,129,891 A 7/1992 Young
5,135,599 A 8/1992 Martin et al.
5,149,330 A 9/1992 Brightbill
5,167,623 A 12/1992 Cianci et al.
5,188,593 A 2/1993 Martin
5,195,962 A 3/1993 Martin et al.
5,207,650 A 5/1993 Martin
5,267,958 A 12/1993 Buchbinder et al.
5,295,970 A 3/1994 Clinton et al.
5,306,247 A 4/1994 Pfenninger
5,328,472 A 7/1994 Steinke et al.
5,350,358 A 9/1994 Martin
5,364,377 A 11/1994 O'Neil
5,368,567 A 11/1994 Lee
5,370,615 A 12/1994 Johnson
5,378,230 A 1/1995 Mahurkar
5,380,290 A 1/1995 Makower et al.
5,389,087 A 2/1995 Miraki
5,405,341 A 4/1995 Martin
5,439,449 A 8/1995 Mapes et al.
5,443,457 A 8/1995 Ginn et al.
5,489,271 A 2/1996 Andersen
5,573,520 A 11/1996 Schwartz et al.
5,683,370 A 11/1997 Luther et al.
5,718,678 A 2/1998 Fleming, III
5,772,636 A 6/1998 Brimhall et al.
5,885,251 A 3/1999 Luther
5,919,164 A 7/1999 Andersen
5,947,940 A 9/1999 Beisel
5,957,893 A 9/1999 Luther et al.
6,066,489 A 5/2000 Fields et al.
6,074,379 A 6/2000 Prichard
6,206,849 B1 3/2001 Martin et al.
6,377,856 B1 4/2002 Carson
6,475,187 B1 11/2002 Gerberding
6,606,515 B1 8/2003 Windheuser et al.
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 5/2008 Katoh et al.
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 4/2010 Brimhall
7,722,567 B2 5/2010 Tal
D617,893 S 6/2010 Bierman et al.
D624,643 S 9/2010 Bierman et al.
7,819,889 B2 10/2010 Healy et al.
7,857,788 B2 12/2010 Racz
D630,729 S 1/2011 Bierman et al.
7,909,797 B2 3/2011 Kennedy, II et al.
7,909,811 B2 3/2011 Agro et al.
7,922,696 B2 4/2011 Tal et al.
7,938,820 B2 5/2011 Webster et al.
7,967,834 B2 6/2011 Tal et al.
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 2/2014 Tal et al.
8,672,888 B2 3/2014 Tal
8,696,645 B2 4/2014 Tal et al.
8,784,362 B2 7/2014 Boutilette et al.
8,827,958 B2 9/2014 Bierman et al.
8,876,704 B2 11/2014 Golden et al.
8,882,713 B1 11/2014 Call et al.
8,900,192 B2 12/2014 Anderson et al.
8,900,207 B2 12/2014 Uretsky
8,915,884 B2 12/2014 Tal et al.
8,956,327 B2 2/2015 Bierman et al.
9,023,093 B2 5/2015 Pal
9,138,252 B2 9/2015 Bierman et al.
9,180,275 B2 11/2015 Helm
9,265,920 B2 2/2016 Rundquist et al.
9,272,121 B2 3/2016 Piccagli
9,522,254 B2 12/2016 Belson
9,554,785 B2 1/2017 Walters et al.
9,566,087 B2 2/2017 Bierman et al.
9,675,784 B2 6/2017 Belson
9,713,695 B2 7/2017 Bunch et al.
9,764,117 B2 9/2017 Bierman et al.
9,770,573 B2 9/2017 Golden et al.
9,814,861 B2 11/2017 Boutillette et al.
9,820,845 B2 11/2017 von Lehe et al.
9,861,383 B2 1/2018 Clark
9,884,169 B2 2/2018 Bierman et al.
9,889,275 B2 2/2018 Voss et al.
9,913,585 B2 3/2018 McCaffrey et al.
9,913,962 B2 3/2018 Tal et al.
9,981,113 B2 5/2018 Bierman
10,010,312 B2 7/2018 Tegels
10,065,020 B2 9/2018 Gaur
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,806,901 B2 10/2020 Burkholz et al.
2002/0040231 A1 4/2002 Wysoki
2002/0198492 A1 12/2002 Miller et al.
2003/0036712 A1 2/2003 Heh et al.
2003/0060863 A1 3/2003 Dobak
2003/0088212 A1 5/2003 Tal

(56) References Cited

U.S. PATENT DOCUMENTS

2003/0100849 A1 5/2003 Jang
2003/0153874 A1 8/2003 Tal
2003/0158514 A1 8/2003 Tal
2004/0116901 A1 6/2004 Appling
2004/0122418 A1 6/2004 Voorhees
2004/0167478 A1* 8/2004 Mooney ............ A61M 25/0097 604/264
2004/0193093 A1 9/2004 Desmond
2004/0199122 A1 10/2004 Bierman et al.
2004/0230178 A1 11/2004 Wu
2005/0004554 A1 1/2005 Osborne
2005/0245882 A1 11/2005 Elkins et al.
2005/0261665 A1 11/2005 Voorhees
2005/0283221 A1 12/2005 Mann et al.
2006/0009740 A1 1/2006 Higgins et al.
2006/0015086 A1 1/2006 Rasmussen et al.
2006/0074380 A1 4/2006 Mogensen et al.
2006/0116629 A1 6/2006 Tal et al.
2006/0129100 A1 6/2006 Tal
2006/0129130 A1 6/2006 Tal et al.
2007/0078412 A1 4/2007 McGuckin et al.
2008/0045894 A1 2/2008 Perchik et al.
2008/0125744 A1 5/2008 Treacy
2008/0125748 A1 5/2008 Patel
2008/0255447 A1 10/2008 Bourang et al.
2008/0262430 A1 10/2008 Anderson et al.
2008/0262431 A1 10/2008 Anderson et al.
2008/0294111 A1 11/2008 Tal et al.
2008/0306465 A1 12/2008 Bailey et al.
2008/0312578 A1 12/2008 DeFonzo et al.
2009/0062772 A1 3/2009 Wakeford et al.
2009/0221961 A1 9/2009 Tal et al.
2009/0270889 A1 10/2009 Tal et al.
2010/0125249 A1 5/2010 Rosenberg et al.
2010/0256487 A1 10/2010 Hawkins et al.
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0144620 A1 6/2011 Tal
2011/0152836 A1 6/2011 Riopelle et al.
2011/0202006 A1 8/2011 Bierman et al.
2011/0251559 A1 10/2011 Tal et al.
2011/0270192 A1 11/2011 Anderson et al.
2011/0319825 A1 12/2011 Goral et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0220942 A1 8/2012 Hall et al.
2012/0232498 A1 9/2012 Ma et al.
2012/0239005 A1 9/2012 Conway et al.
2012/0283640 A1 11/2012 Anderson et al.
2012/0316500 A1 12/2012 Bierman et al.
2013/0053826 A1 2/2013 Shevgoor
2013/0123704 A1 5/2013 Bierman et al.
2013/0150793 A1* 6/2013 Beissel ................. A61M 39/06 604/171
2013/0158338 A1 6/2013 Kelly et al.
2013/0188291 A1 7/2013 Vardiman
2013/0218082 A1* 8/2013 Hyer ................. A61M 25/0097 604/256
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0100552 A1 4/2014 Gallacher et al.
2014/0207052 A1 7/2014 Tal et al.
2014/0207069 A1 7/2014 Bierman et al.
2014/0214005 A1 7/2014 Belson
2014/0257111 A1 9/2014 Yamashita et al.
2014/0276432 A1 9/2014 Bierman et al.
2014/0276599 A1 9/2014 Cully et al.
2015/0051536 A1 2/2015 Mendels et al.
2015/0080939 A1 3/2015 Adams et al.
2015/0112310 A1 4/2015 Call et al.
2015/0126930 A1 5/2015 Bierman et al.
2015/0148595 A1 5/2015 Bagwell et al.
2015/0190168 A1 7/2015 Bierman et al.
2015/0196210 A1 7/2015 McCaffrey et al.
2015/0224287 A1 8/2015 Bian et al.
2015/0283357 A1 10/2015 Lampropoulos et al.
2015/0297868 A1 10/2015 Tal et al.
2015/0320969 A1 11/2015 Haslinger et al.
2015/0351793 A1 12/2015 Bierman et al.
2015/0359549 A1 12/2015 Lenker et al.
2015/0359998 A1 12/2015 Carmel et al.
2016/0008577 A1 1/2016 Wright et al.
2016/0067449 A1 3/2016 Misener et al.
2016/0082223 A1 3/2016 Barnell
2016/0114124 A1 4/2016 Tal
2016/0220786 A1* 8/2016 Mitchell ........... A61M 25/0029
2016/0306393 A1 10/2016 Huitema
2016/0325073 A1 11/2016 Davies et al.
2016/0338728 A1 11/2016 Tal
2016/0346503 A1 12/2016 Jackson et al.
2017/0035990 A1 2/2017 Swift
2017/0043126 A1 2/2017 Jones et al.
2017/0072165 A1 3/2017 Lim et al.
2017/0120000 A1 5/2017 Osypka et al.
2017/0128700 A1 5/2017 Roche Rebollo
2017/0143890 A1 5/2017 Nardeo
2017/0172653 A1 6/2017 Urbanski et al.
2017/0239443 A1 8/2017 Abitabilo et al.
2017/0273628 A1 9/2017 Ofek et al.
2017/0273713 A1 9/2017 Shah et al.
2017/0296792 A1 10/2017 Ornelas Vargas et al.
2017/0326339 A1 11/2017 Bailey et al.
2017/0326349 A1 11/2017 Pagano, II et al.
2017/0361070 A1 12/2017 Hivert
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0214674 A1* 8/2018 Ebnet ..................... A61B 90/40
2018/0296799 A1 10/2018 Horst et al.
2018/0296804 A1 10/2018 Bierman
2019/0015646 A1 1/2019 Matlock et al.
2019/0060616 A1 2/2019 Solomon
2019/0076167 A1 3/2019 Fantuzzi et al.
2019/0134349 A1 5/2019 Cohn et al.
2019/0201665 A1 7/2019 Turpin
2019/0255294 A1 8/2019 Mitchell et al.
2019/0276268 A1 9/2019 Akingba
2019/0321590 A1 10/2019 Burkholz et al.
2020/0016374 A1 1/2020 Burkholz et al.
2020/0121211 A1 4/2020 Tutino
2021/0069471 A1 3/2021 Howell
2021/0121661 A1 4/2021 Howell
2021/0121667 A1 4/2021 Howell
2021/0128879 A1 5/2021 Seidenberger
2021/0322729 A1 10/2021 Howell
2021/0330941 A1 10/2021 Howell et al.
2021/0330942 A1 10/2021 Howell
2021/0361915 A1 11/2021 Howell et al.
2021/0402142 A1 12/2021 Howell et al.
2021/0402149 A1 12/2021 Howell
2021/0402153 A1 12/2021 Howell et al.
2022/0001138 A1 1/2022 Howell
2022/0032013 A1 2/2022 Howell et al.
2023/0256199 A1 8/2023 Howell
2023/0285719 A1 9/2023 Salamini et al.

FOREIGN PATENT DOCUMENTS

EP 2061385 A1 5/2009
EP 1458437 B1 3/2010
EP 2248549 A2 11/2010
EP 2319576 A1 5/2011

(56) References Cited

FOREIGN PATENT DOCUMENTS

| | | | |
|---|---|---|---|
| EP | 2366422 | A1 | 9/2011 |
| EP | 2486880 | A2 | 8/2012 |
| EP | 2486881 | A2 | 8/2012 |
| EP | 2486951 | A2 | 8/2012 |
| EP | 2512576 | A2 | 10/2012 |
| EP | 2152348 | B1 | 2/2015 |
| EP | 2896424 | A1 | 7/2015 |
| EP | 3093038 | B1 | 5/2019 |
| EP | 2260897 | B1 | 9/2019 |
| GB | 1273547 | A | 5/1972 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 2003008020 | A1 | 1/2003 |
| WO | 2003057272 | A2 | 7/2003 |
| WO | 2003066125 | A2 | 8/2003 |
| WO | 2004050144 | A2 | 6/2004 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015/166157 | A1 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2017127074 | A1 | 7/2017 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/034320 | A1 | 2/2019 |
| WO | 2019/040801 | A1 | 2/2019 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2022133297 | A1 | 6/2022 |
| WO | 2023158613 | A1 | 8/2023 |
| WO | 2023158709 | A1 | 8/2023 |

OTHER PUBLICATIONS

PCT/US2020/056364 filed Oct. 19, 2020 International Search Report and Written Opinion dated Jan. 19, 2021.

PCT/US2020/056864 filed Oct. 22, 2020 International Preliminary Report on Patentability dated Apr. 26, 2022.

PCT/US2020/056864 filed Oct. 22, 2020 International Search Report and Written Opinion dated Jan. 14, 2021.

PCT/US2020/057397 filed Oct. 26, 2020 International Search Report and Written Opinion dated Mar. 10, 2021.

PCT/US2021/036445 filed Jun. 8, 2021 International Search Report and Written Opinion dated Dec. 21, 2021.

PCT/US2021/039398 filed Jun. 28, 2021 International Search Report and Written Opinion dated Nov. 5, 2021.

U.S. Appl. No. 17/074,405, filed Oct. 19, 2020 Restriction Requirement dated Jan. 17, 2023.

U.S. Appl. No. 17/077,728, filed Oct. 22, 2020 Final Office Action dated Jun. 14, 2022.

U.S. Appl. No. 17/077,728, filed Oct. 22, 2020 Non-Final Office Action dated Feb. 15, 2023.

U.S. Appl. No. 17/077,728, filed Oct. 22, 2020 Non-Final Office Action dated Feb. 9, 2022.

U.S. Appl. No. 17/080,578, filed Oct. 26, 2020 Restriction Requirement dated Dec. 15, 2022.

U.S. Appl. No. 17/080,578, filed Oct. 26, 2020 Advisory Action dated Apr. 11, 2024.

U.S. Appl. No. 17/080,578, filed Oct. 26, 2020 Non-Final Office Action dated Jun. 11, 2024.

U.S. Appl. No. 17/342,285, filed Jun. 8, 2021 Advisory Action dated Jul. 25, 2024.

U.S. Appl. No. 17/342,285, filed Jun. 8, 2021 Final Office Action dated Apr. 25, 2024.

U.S. Appl. No. 17/360,746, filed Jun. 28, 2021 Non-Final Office Action dated Mar. 19, 2024.

PCT/US2023/012931 filed Feb. 13, 2023 International Search Report and Written Opinion dated May 25, 2023.

PCT/US2023/013165 filed Feb. 15, 2023 International Search Report and Written Opinion dated Jun. 13, 2023.

U.S. Appl. No. 17/074,405, filed Oct. 19, 2020 Non-Final Office Action dated Mar. 31, 2023.

U.S. Appl. No. 17/077,728, filed Oct. 22, 2020 Final Office Action dated Aug. 28, 2023.

U.S. Appl. No. 17/080,578, filed Oct. 26, 2020 Non-Final Office Action dated Mar. 31, 2023.

U.S. Appl. No. 17/342,285, filed Jun. 8, 2021 Non-Final Office Action dated Aug. 1, 2023.

U.S. Appl. No. 17/342,285, filed Jun. 8, 2021 Restriction Requirement dated May 2, 2023.

U.S. Appl. No. 17/360,746, filed Jun. 28, 2021 Non-Final Office Action dated Jun. 29, 2023.

EP 20878324.1 filed Mar. 11, 2022 Extended European Search Report dated Jan. 3, 2024.

EP 20882316.1 filed Apr. 21, 2022 Extended European Search Report dated Oct. 16, 2023.

U.S. Appl. No. 17/074,405, filed Oct. 19, 2020 Final Office Action dated Jan. 18, 2024.

U.S. Appl. No. 17/077,728, filed Oct. 22, 2020 Examiner's Answer dated Mar. 7, 2024.

U.S. Appl. No. 17/080,578, filed Oct. 26, 2020 Final Office Action dated Feb. 27, 2024.

U.S. Appl. No. 17/342,285, filed Jun. 8, 2021 Non-Final Office Action dated Dec. 22, 2023.

U.S. Appl. No. 17/360,746, filed Jun. 28, 2021 Final Office Action dated Nov. 6, 2023.

U.S. Appl. No. 17/074,405, filed Oct. 19, 2020 Non-Final Office Action dated Aug. 14, 2024.

U.S. Appl. No. 17/074,405, filed Oct. 19, 2020 Non-Final Office Action dated Feb. 5, 2025.

U.S. Appl. No. 17/080,578, filed Oct. 26, 2020 Final Office Action dated Jan. 10, 2025.

U.S. Appl. No. 17/342,285, filed Jun. 8, 2021 Non-Final Office Action dated Sep. 28, 2024.

(56) References Cited

OTHER PUBLICATIONS

U.S. Appl. No. 17/360,746, filed Jun. 28, 2021 Final Office Action dated Aug. 21, 2024.
U.S. Appl. No. 17/342,285, filed Jun. 8, 2021 Final Office Action dated Mar. 7, 2025.
U.S. Appl. No. 17/360,746, filed Jun. 28, 2021 Examiner's Answer dated Mar. 13, 2025.
U.S. Appl. No. 17/077,728, filed Oct. 22, 2020 Board Decision dated Aug. 20, 2025.
U.S. Appl. No. 17/077,728, filed Oct. 22, 2020 Notice of Allowance dated Dec. 17, 2025.
U.S. Appl. No. 17/080,578, filed Oct. 26, 2020 Non-Final Office Action dated Oct. 17, 2025.
U.S. Appl. No. 17/342,285, filed Jun. 8, 2021 Non-Final Office Action dated Aug. 27, 2025.
U.S. Appl. No. 17/360,746, filed Jun. 28, 2021 Board Decision dated Feb. 2, 2026.
U.S. Appl. No. 18/109,103, filed Feb. 13, 2023 Restriction Requirement dated Jan. 15, 2026.
U.S. Appl. No. 17/342,285, filed Jun. 8, 2021 Final Office Action dated Mar. 6, 2026.
U.S. Appl. No. 17/360,746, filed Jun. 28, 2021 Notice of Allowance dated Apr. 27, 2026.
U.S. Appl. No. 18/109,103 filed Feb. 13, 2023 Non-Final Office Action dated Apr. 7, 2026.

* cited by examiner 104
408
120
106
150
122
409
104
416
120
407
150

104
305A
540
409
407
305A
514
513
118
519
150
340
550
408
122

6B
118

610
6B 118
606
605

610
607

104
307
328
306
330
326
8A
8B
8C
8D 104, 326
305A
834

104, 330
832
305C
305B 104, 328

900
905A
904
distal
920
908
911A
910A
906
940
924
910A
911A
918
950
proximal
910

1014
1009
1004
1000
distal
1020
1006
1008
proximal
1010
1018
1019
1010A
1011A 150
1005A
1004
1005
distal
1006
1050
1012
1012A
1010
1011
1018
150
1019
1013
proximal 1110
150
1110
1106
proximal
1120
1130
distal
1014

CENTRAL CATHETERS, ASSEMBLIES, AND METHODS THEREOF

PRIORITY

This application claims the benefit of priority to U.S. Provisional Application No. 63/310,533, filed Feb. 15, 2022, which is incorporated by reference in its entirety into this application.

BACKGROUND

The Seldinger technique utilizes a number of steps and medical devices (e.g., a needle, a scalpel, a guidewire, an introducer sheath, a dilator, etc.) for introducing central catheters such as central venous catheters ("CVCs") and the like into patients and advancing such catheters through vasculatures of the patients. While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter into a patient and advancing the catheter through a vasculature thereof.

In some instances, the needle may be unnecessarily long so as to extend between a Luer connector of an extension leg to the distal end of the catheter tube. The long length of the needle requires extensive care in handling of the needle to prevent bending of the needle or other damage. The long needle length may also cause a significant delay in obtaining a blood flash and in some instances the long needle length may cause intraluminal blood clots.

Disclosed herein are central catheters and related devices, assemblies for providing a shortened needle and methods for inserting a central catheter having a shortened needle.

SUMMARY

Disclosed herein is a central catheter, including a catheter tube configured for advancement along a vasculature of a patient, where the catheter tube includes: (i) a number of catheter-tube lumens extending along the catheter tube; (ii) a number of extension legs equal to the number of catheter-tube lumens, where each extension leg is in fluid communication with a corresponding catheter-tube lumen; (iii) a needle hub coupled with the catheter tube, where the needle hub includes a needle-hub lumen configured for advancement of a needle therethrough. The needle hub further includes a septum disposed across a proximal portion of the needle-hub lumen, where the septum is configured define a fluid tight seal with the needle when the needle is disposed within the needle-hub lumen, and prevent fluid flow through the proximal portion of the needle-hub lumen when the needle is not disposed within the needle-hub lumen. The needle hub is coupled with the catheter tube such that the needle-hub lumen is in fluid communication with one of the catheter-tube lumens.

In some embodiments, the needle-hub lumen is parallel with the catheter tube along a distal portion of the needle hub. The needle-hub lumen may also be colinear with the one of the catheter-tube lumens along the distal portion of the needle hub.

In some embodiments, the needle hub further includes one or more suture wings for securing the needle hub to the patient. The one or more suture wings may define a patient contact surface of the hub, and in some embodiments, the patient contact surface is parallel with the needle-hub lumen.

In some embodiments, the catheter includes a manifold hub defining the fluid communication between each extension leg and its corresponding catheter-tube lumen and the extension legs are attached to the manifold hub.

In some embodiments, the needle hub includes the manifold hub incorporated therein such that the extension legs are attached to the needle hub. In some embodiments, each extension leg includes a Luer connector at a proximal end thereof.

In some embodiments, each extension leg may be attached to the needle hub at an angle with respect to the needle-hub lumen. Each extension leg may also be attached to the needle hub at an angle with respect to the patient contact surface. In further embodiments, the extension legs are attached to the needle hub within a plane.

In some embodiments, the number of lumens may include (i) a primary lumen extending distally to a distal end of the catheter tube; (ii) a secondary lumen extending distally to a first side port of the catheter tube; and (iii) a tertiary lumen extending distally to a second side port, where the second side port is disposed proximal the first side port.

In some embodiments, a material of the septum is one of a silicone rubber, ethylene propylene diene terpolymer (EPDM), or a polyurethane, and in some embodiments, the hub and the septum are composed of the same material.

In some embodiments, the septum is formed integral to the hub during the hub forming process, and in some embodiments, the septum includes a preformed slit configured for insertion of the needle therethrough.

Also disclosed herein is a central catheter assembly that includes any of the embodiments of the central catheter summarized above and a needle preloaded in the central catheter, where the needle is disposed within the needle-hub lumen and the primary catheter-tube lumen. The needle may be positioned within the primary catheter-tube lumen so that the needle extends beyond the distal end of the catheter tube to facilitate a percutaneous puncture with the needle.

In some embodiments, the needle includes a lubricant disposed on an outside surface of the needle to facilitate a sliding engagement of the needle with the septum.

In some embodiments, the number of extension legs includes a primary extension leg in fluid communication with the primary lumen, and the assembly further includes a preloaded guidewire disposed within the primary extension leg.

Also disclosed herein is a method for introducing a central catheter into a blood vessel of a patient. The method includes providing a central catheter that includes a catheter tube having a catheter-tube lumen extending therethrough to a distal end of the catheter tube and a needle hub coupled with the catheter tube. The needle hub includes a needle-hub lumen configured for advancement of a needle therethrough and a septum disposed across a proximal portion of the needle-hub lumen. The septum is configured to (i) define a fluid tight seal with the needle when the needle is disposed within the needle-hub lumen and (ii) prevent fluid flow through the proximal portion of the needle-hub lumen when the needle is not disposed within the needle-hub lumen. The needle hub is coupled with the catheter tube such that the needle-hub lumen is in fluid communication with the catheter-tube lumen. The method further includes (i) inserting the catheter tube through a skin of the patient to the blood vessel such that the distal end of the catheter is disposed within the blood vessel, where the catheter-tube lumen includes a needle disposed therein; (ii) advancing the catheter tube along the needle to advance the catheter tube further into the blood vessel lumen; (iii) and withdrawing the needle from the catheter-tube lumen.

In some embodiments, the method further includes inserting the needle through the needle-hub lumen into the catheter-tube lumen.

In some embodiments, the method further includes aspirating blood with a syringe connected to the needle before withdrawing the needle from the catheter-tube lumen, thereby confirming a distal tip of the needle is disposed within the blood-vessel lumen.

Also disclosed herein is a central catheter hub, that includes a hub body defining a proximal end and a distal end, where the hub body is configured to couple with a central catheter tube having a number of catheter-tube lumens extending therethrough. The central catheter hub further includes a needle-hub lumen extending through the hub body configured for advancement of a needle therethrough, where the needle-hub lumen is in fluid communication one of the number of catheter-tube lumens. The central catheter hub further includes a septum disposed across a proximal portion of the needle-hub lumen, where the septum is configured to (i) define a fluid tight seal with a needle when the needle is disposed within the needle-hub lumen, and (ii) prevent fluid flow through the proximal portion of the needle-hub lumen when the needle is not disposed within the needle-hub lumen. The central catheter hub further includes one or more suture wings extending away from the hub body for securing the needle hub to the patient.

In some embodiments, the one or more suture wings define a patient contact surface of the hub, and the patient contact surface is parallel with the needle-hub lumen.

In some embodiments, the hub body is configured to couple with the catheter tube so that the needle-hub lumen is parallel with the catheter tube along a distal portion of the hub body. In some embodiments, the hub body is configured to couple with the catheter tube so that the needle-hub lumen is colinear with the one of the number of catheter-tube lumens along a distal portion of the hub body.

In some embodiments, the hub body is configured to couple with a number of extension legs equal to the number of catheter-tube lumens so that each extension leg is in fluid communication with a corresponding catheter-tube lumen.

In some embodiments, the hub body is configured is configured to couple with the extension legs so that each extension leg extends away from the proximal end at an angle with respect to the needle-hub lumen.

In some embodiments, the hub body is configured to couple with the extension legs so that each extension leg extends away from the proximal end at an angle with respect to the patient contact surface.

In some embodiments, a material of the septum is one of a silicone rubber, ethylene propylene diene terpolymer (EPDM), or a polyurethane, and in some embodiments, the hub body and the septum are composed of the same material. In some embodiments, the septum is formed integral to the hub body during the hub body forming process, and in some embodiments, the septum includes a preformed slit configured for insertion of the needle therethrough.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
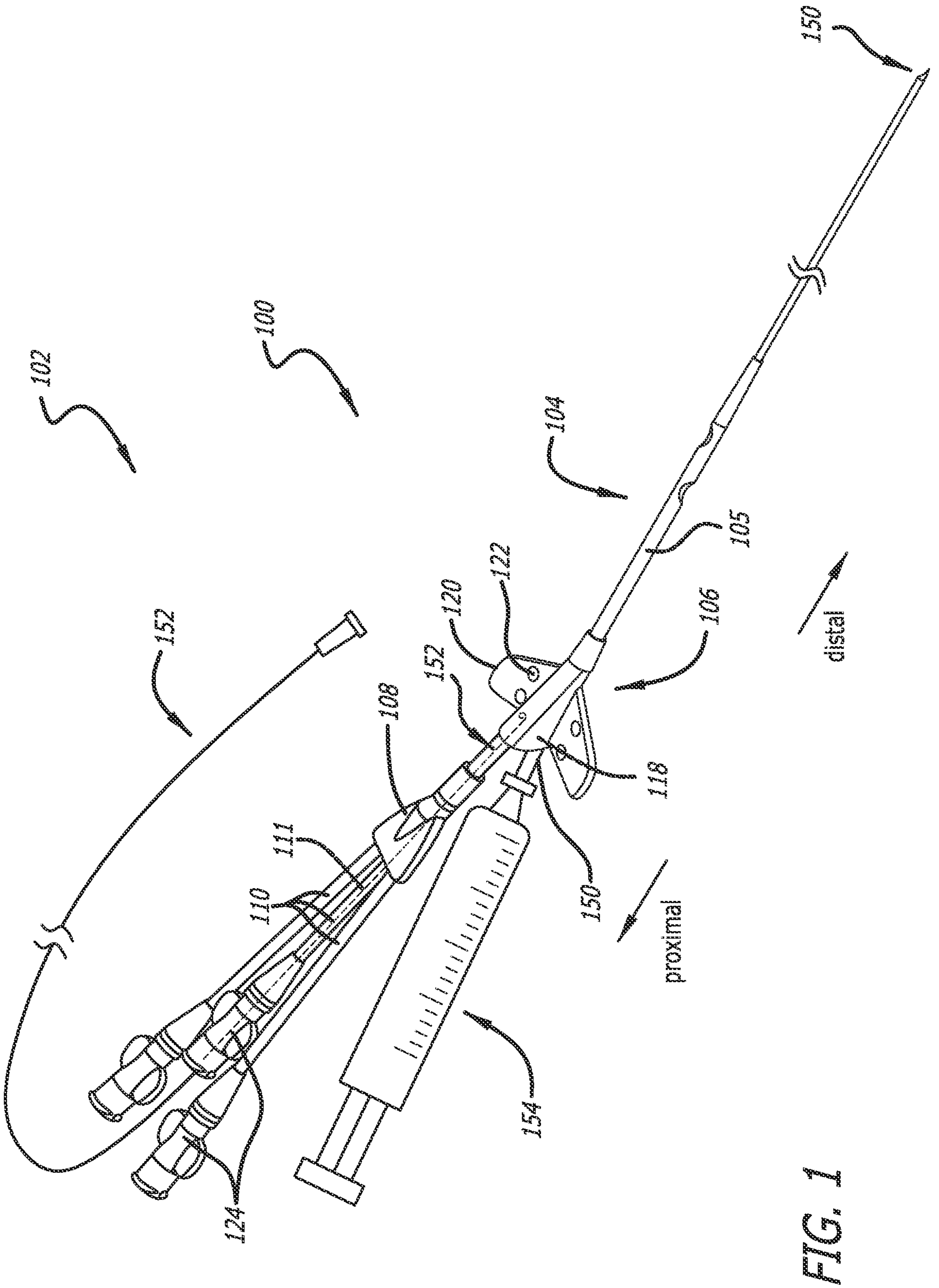
FIG. 1 illustrates a central catheter assembly in an assembled, ready-to-introduce state in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, “first,” “second,” and “third” features or steps need not necessarily appear in that order, and the particular embodiments including such features or steps need not necessarily be limited to the three features or steps. Labels such as “left,” “right,” “top,” “bottom,” “front,” “back,” and the like are used for convenience and are not intended to imply, for example, any particular fixed location, orientation, or direction. Instead, such labels are used to reflect, for example, relative location, orientation, or directions. Singular forms of “a,” “an,” and “the” include plural references unless the context clearly dictates otherwise.

With respect to “proximal,” a “proximal portion” or a “proximal-end portion” of, for example, a catheter includes a portion of the catheter intended to be near a clinician when the catheter is used on a patient. Likewise, a “proximal length” of, for example, the catheter includes a length of the catheter intended to be near the clinician when the catheter is used on the patient. A “proximal end” of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to “distal,” a “distal portion” or a “distal-end portion” of, for example, a catheter includes a portion of the catheter intended to be near or in a patient when the catheter is used on the patient. Likewise, a “distal length” of, for example, the catheter includes a length of the catheter intended to be near or in the patient when the catheter is used on the patient. A “distal end” of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

The phrases “connected to” and “coupled with” refer to any form of interaction between two or more entities, including mechanical, electrical, magnetic, electromagnetic, fluid, signal, communicative (including wireless), and thermal interaction. Two components may be connected to or coupled with each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

As set forth above, there is a need to reduce the number of steps and medical devices involved in introducing a catheter into a patient and advancing the catheter through a vasculature thereof. Disclosed herein are central catheters, central catheter assemblies, and methods thereof that address the foregoing.

Figure 2:
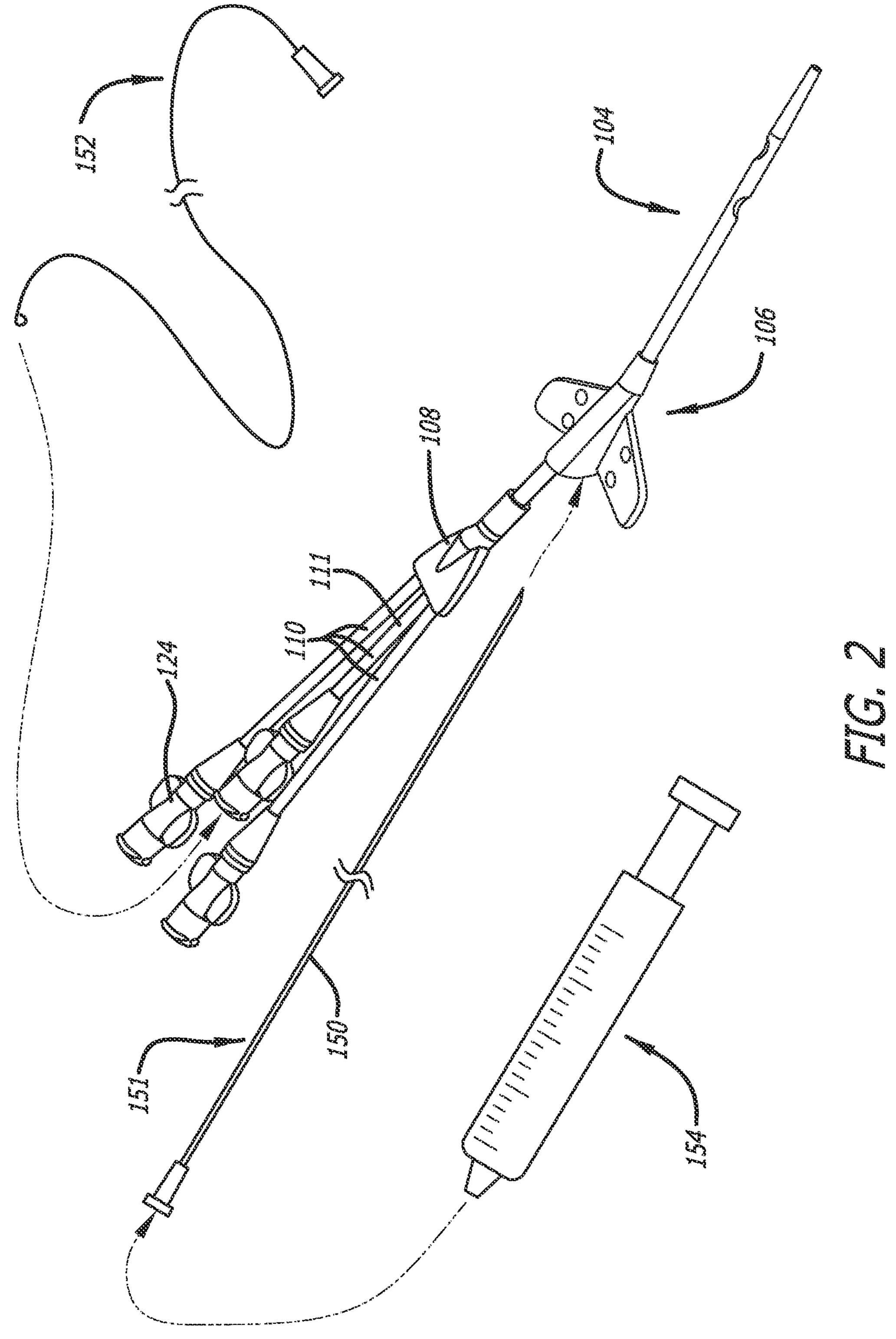
FIG. 2 illustrates the central catheter assembly in a disassembled state in accordance with some embodiments.

FIGS. 1 and 2 illustrate a central catheter assembly 102 in a ready-to-introduce assembled state and a non-assembled state, respectively, in accordance with some embodiments. The catheter assembly 102 generally includes a catheter 100 (e.g., a central venous catheter or a rapid insertion central catheter), and a needle 150 disposed within the catheter 100.

Optionally, the central catheter assembly 102 includes a guidewire 152 preloaded in the catheter 100, a syringe 154 coupled to a hub of the needle 150, or both the guidewire 152 and the syringe 154 in the ready-to-introduce state of the central catheter assembly 102. In a packaged state of the central catheter assembly 102, the central catheter assembly 102 resembles the ready-to-introduce state of the central catheter assembly 102; however, if the syringe 154 is present in a package including the central catheter assembly 102, the syringe 154 need not be coupled to the hub of the needle 150. Indeed, the syringe 154 can be packaged alongside a remainder of the central catheter assembly 102 in the packaged state of the central catheter assembly 102.

The catheter 100 generally includes a catheter tube 104 coupled with a number of extension legs 110 via a manifold hub 108 where each extension leg includes an extension-leg lumen 111. The catheter tube 104 includes a number of catheter-tube lumens 105 extending along the catheter tube 104 where the number of catheter-tube lumens 105 equals the number of the extension legs 110. The extension legs 110 are coupled with the catheter tube 104 such that each extension-leg lumen 111 is in fluid communication with a corresponding catheter-tube lumen 105. Each extension leg 110 includes a Luer connector 124 at a proximal end of each extension leg 110.

The catheter 100 includes a needle hub 106 coupled with the catheter tube 104. The needle hub 106 includes one or more suture wings 120 having one or more through-holes 122. The needle 150 is inserted into the catheter 100 via the needle hub 106 so as to extend along the catheter tube 104 to a distal end of the catheter tube 104. More specifically, the needle 150 is inserted into a catheter-tube lumen 105 (e.g., a primary catheter-tube lumen) so that a distal tip of the needle 150 extends beyond the distal end of the catheter tube 104. The needle hub 106 includes a septum 118 and the needle 150 is inserted through the septum 118. The needle 150 may optionally include a lubricant 151 disposed along an outside surface of the needle 150 to facilitate a sliding engagement of the needle 150 with the septum 118, i.e., the lubricant 151 may reduce a friction between the needle 150 and the septum 118.

The guidewire 152 may be inserted into the catheter 100 by way of an extension-leg lumen 111 via the corresponding Luer connector 124 in the optional ready-to-introduce state of the central catheter assembly 102. More specifically, the guidewire 152 is inserted into the extension-leg lumen 111 that is coupled with the primary catheter-tube lumen. Such placement of the guidewire 152 in the ready-to-introduce state of the central catheter assembly 102 enables the guidewire 152 to be immediately advanced into a blood-vessel lumen of a patient after a percutaneous puncture with the needle 150 and withdrawal thereof from the catheter 100.

The foregoing placement of the guidewire 152 in the ready-to-introduce state of the central catheter assembly 102 is advantageous over placement of the guidewire 152 in the needle 150 because it allows the guidewire 152 to have a larger diameter than that allowed by the needle 150, which larger diameter provides more stability for the catheter tube 104 when maneuvered over the guidewire 152.

The catheter 100 can be a monoluminal catheter or a multiluminal catheter such as a diluminal catheter, a triluminal catheter, a tetraluminal catheter, a pentaluminal catheter, or a hexaluminal catheter. Accordingly, the manifold hub 108 is either not furcated in accordance with the monoluminal catheter or furcated in accordance with a number of lumens extending through the catheter 100. For example, the manifold hub 108 can be bifurcated for the diluminal catheter or trifurcated for the triluminal catheter. Depending upon a chosen method of manufacturing, the manifold hub 108 can be molded over a number of core pins for a number of fluid pathways longitudinally extending through the manifold hub 108 configured to fluidly connect each catheter-tube lumen 105 to a corresponding extension-leg lumen 111. Alternatively, the manifold hub 108 can be molded over a number of cannulas longitudinally extending through the manifold hub 108 configured to fluidly connect each catheter-tube lumen 105 to a corresponding extension-leg lumen 111.

The number of extension legs 110 extend from the manifold hub 108 by way of their distal portions. The number of extension legs 110 is equal to the number of lumens extending through the catheter 100. For example, if the catheter 100 is a monoluminal catheter, one extension leg extends from the manifold hub 108. If the catheter 100 is a diluminal catheter, two extension legs extend from the manifold hub 108. If the catheter 100 is a triluminal catheter, three extension legs extend from the manifold hub 108.

Figure 3:
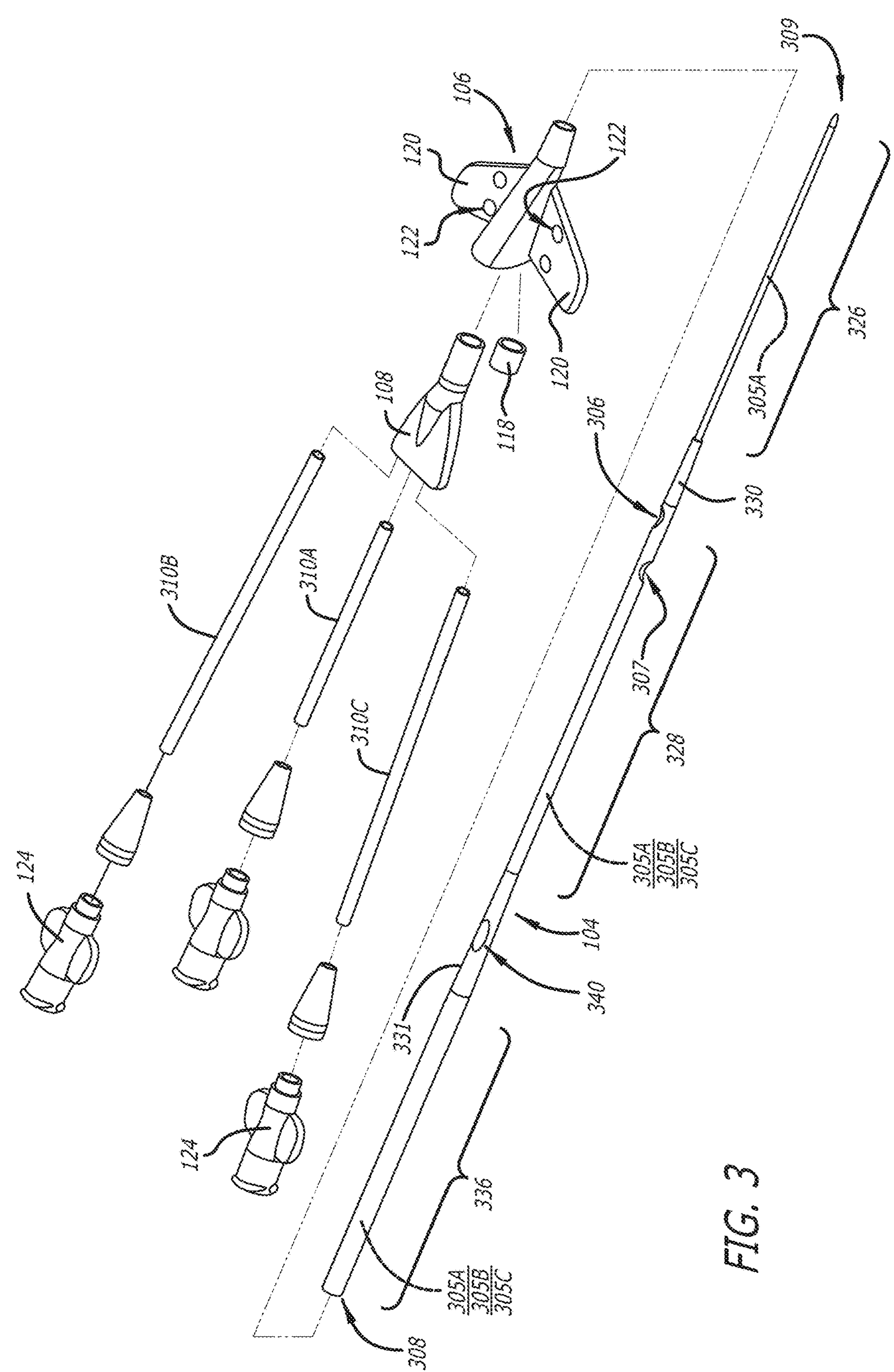
FIG. 3 illustrates a central catheter in a disassembled state in accordance with some embodiments.

FIG. 3 illustrates the catheter 100 in a disassembled state in accordance with some embodiments. In the illustrated embodiment, the catheter 100 is a triluminal catheter including a primary catheter-tube lumen 305A coupled a primary extension leg 310A, a secondary catheter-tube lumen 305B coupled a secondary extension leg 310B, and a tertiary catheter-tube lumen 305C coupled a tertiary extension leg 310C.

In the assembled state of the central catheter assembly 102, the needle 150 is inserted into the primary catheter-tube lumen 305A of the catheter 100 by way of the needle hub 106 in the ready-to-introduce state of the central catheter assembly 102 so that a distal tip of the needle 150 including a bevel extends past the distal end of the catheter tube 104 for a percutaneous puncture with the needle 150.

The catheter tube 104 is illustrated having a first section 326, second section 328 proximal the first section 326, and a third section 336 proximal the second first section 326. In some embodiments, the second section 328 may be larger in diameter than the first section 326 and the third section 336 may be larger in diameter than the second section 328. The catheter tube 104 may include a first tapered transition portion 330 disposed between the first section 326 and the second section 328. The catheter tube 104 may further include a second tapered transition portion 331 disposed between the second section 328 and the third section 336.

The primary catheter-tube lumen 305A extends from a proximal end 308 of the catheter tube 104 to a distal end 309 of the catheter tube 104. The secondary catheter-tube lumen 305B extends from the proximal end 308 to a secondary side port 306, and the tertiary catheter-tube lumen 305B extends from the proximal end 308 to a tertiary side port 307. In some embodiments, the secondary side port 306 may be disposed distal the tertiary side port 307. A needle side port 340 provides needle access to the primary catheter-tube lumen 305A. In some embodiments, the needle side port 340 may be disposed along the second tapered transition portion 331.

Figure 4:
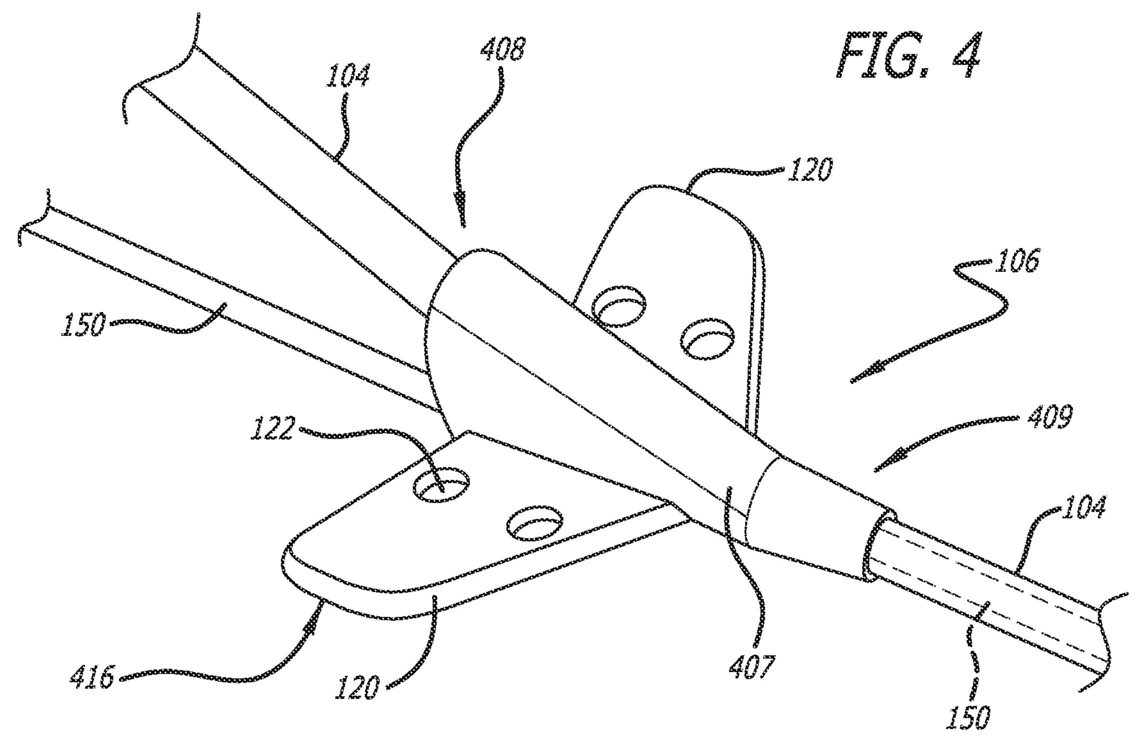
FIG. 4 illustrates a perspective view of a needle hub of the catheter of FIGS. 1-3 including a needle inserted through the needle hub in accordance with some embodiments.
Figure 5:
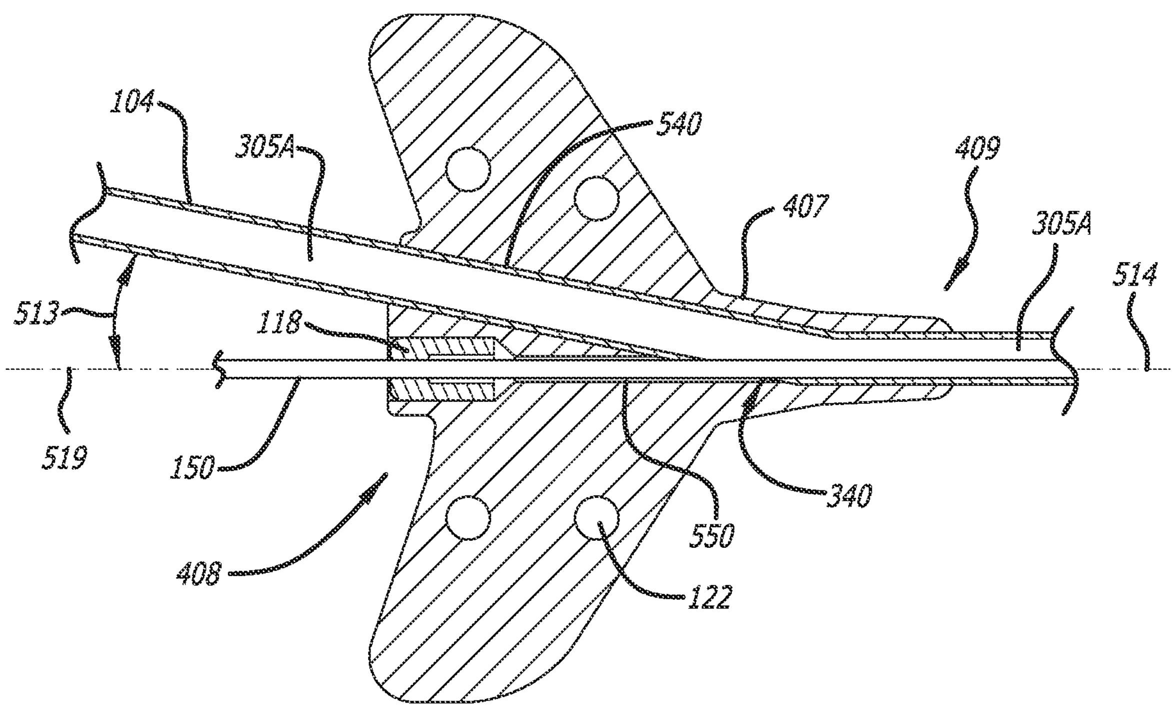
FIG. 5 illustrates a cross-sectional view of the needle hub of FIG. 4 in accordance with some embodiments.

FIGS. 4-5 illustrate the needle hub 106 including the catheter tube 104 and the needle 150. FIG. 4 is top perspective view and FIG. 5 is a top cross-sectional view. The needle hub 106 includes a hub body 407 and the one or more suture wings 120 extending away from the hub body 407. The suture wings 120 include a number of wing through-holes 122 for suturing the needle hub 106 to a patient. Each wing of the one or more suture wings 120 can include a number of through holes 122 (e.g., one, two, three, four or more) for suturing the needle hub 106 to a patient. The hub body 407 and the suture wings 120 may define a patient contact surface 416 of the needle hub 106, where the patient contact surface 416 is disposed along an underside of the needle hub 106. The catheter tube 104 and the needle 150 enter the hub body 407 at the proximal end 408 of the hub body 407 and the exit the hub body 407 at the distal end 409 of the hub body 407. The needle hub may be formed of any suitable moldable material such as a thermal plastic material or an elastomeric material, for example.

Referring to FIG. 5, the hub body 407 includes a needle-hub lumen 550 extending between the proximal end 408 and the distal end 409. The hub body 407 further includes a catheter-tube passageway 540 extending between the proximal end 408 and the distal end 409. The needle-hub lumen 550 and catheter-tube passageway 540 enter the hub body separately and exit the hub body 407 in combination. More specifically, the needle-hub lumen 550 and catheter-tube passageway 540 combine (join together) within the hub body 407 to form a combined passageway at the distal end 409. The needle 150 is inserted through the needle-hub lumen 550. The needle 150 is inserted into the primary catheter-tube lumen 305A via the needle port 340. The needle 150 exits the hub body 407 with the needle disposed within the primary catheter-tube lumen 305A.

The needle-hub lumen 550 and catheter-tube passageway 540 are arranged at the proximal end 408 so that the needle 150 and catheter tube 104 extend proximally away from the needle hub 106 at an angle 513 with respect to each other causing the needle 150 and catheter tube 104 to depart from each other as they extend proximally away from the needle hub 106. More specifically the catheter tube 104 extends proximally away from the needle hub 106 at an angle 513 with respect to a longitudinal axis 519 of the needle-hub lumen 550. In some embodiments, the needle 150 and the catheter tube 104 may depart laterally from each other with respect to the patient contact surface 416, e.g., in a direction parallel to the patient contact surface 416. In some embodiments, the needle 150 and the catheter tube 104 may depart vertically from each other with respect to the patient contact surface 416, e.g., in a direction perpendicular to the patient contact surface 416. In further embodiments, the needle 150 and the catheter tube 104 may depart laterally and vertically from each other.

In some embodiments, the needle-hub lumen 550 is disposed parallel with the catheter tube 104 along a distal portion of the needle hub 106. In other words, the catheter tube 104 disposed parallel with the distal portion of the needle hub 106 may define a longitudinal axis 514, and the longitudinal axis 519 may be parallel with the longitudinal axis 514. In further embodiments, the primary catheter-tube lumen 305A may define the longitudinal axis 514 and the longitudinal axis 514 may be colinear with the longitudinal axis 519.

The needle hub 106 further includes the septum 118 disposed in the needle-hub lumen 550. The septum 118 is configured define a fluid tight seal with the needle 150 when the needle 150 is disposed within the needle-hub lumen 550, and prevent fluid flow through the needle-hub lumen when the needle 150 is withdrawn from (i.e., not disposed within) the needle-hub lumen 550. In some embodiments, the septum 118 is positioned at the proximal end 408 of the hub body 407. Positioning the septum 118 at the proximal end 408 may facilitate swabbing of the septum 118 by the clinician to disinfect the septum 118 therapy preventing microbial ingress to the patient vasculature during insertion of the needle 150.

Figure 6A:
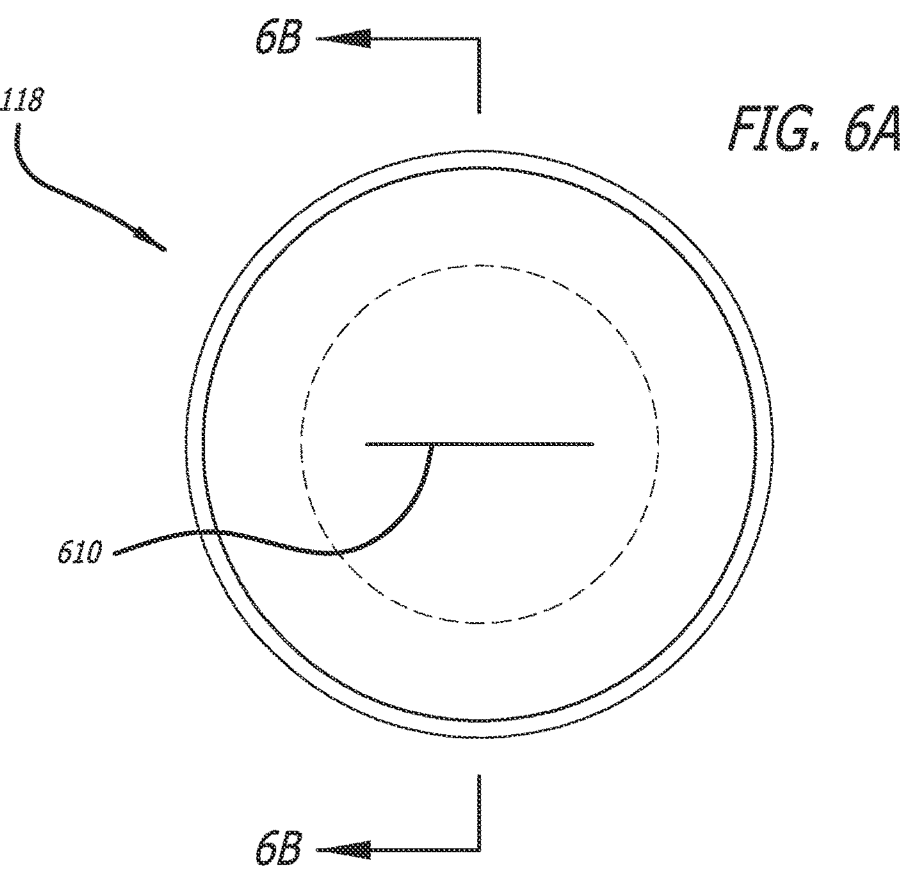
FIG. 6A illustrates a front view of a septum of the needle hub of FIGS. 4-5 in accordance with some embodiments.
Figure 6B:
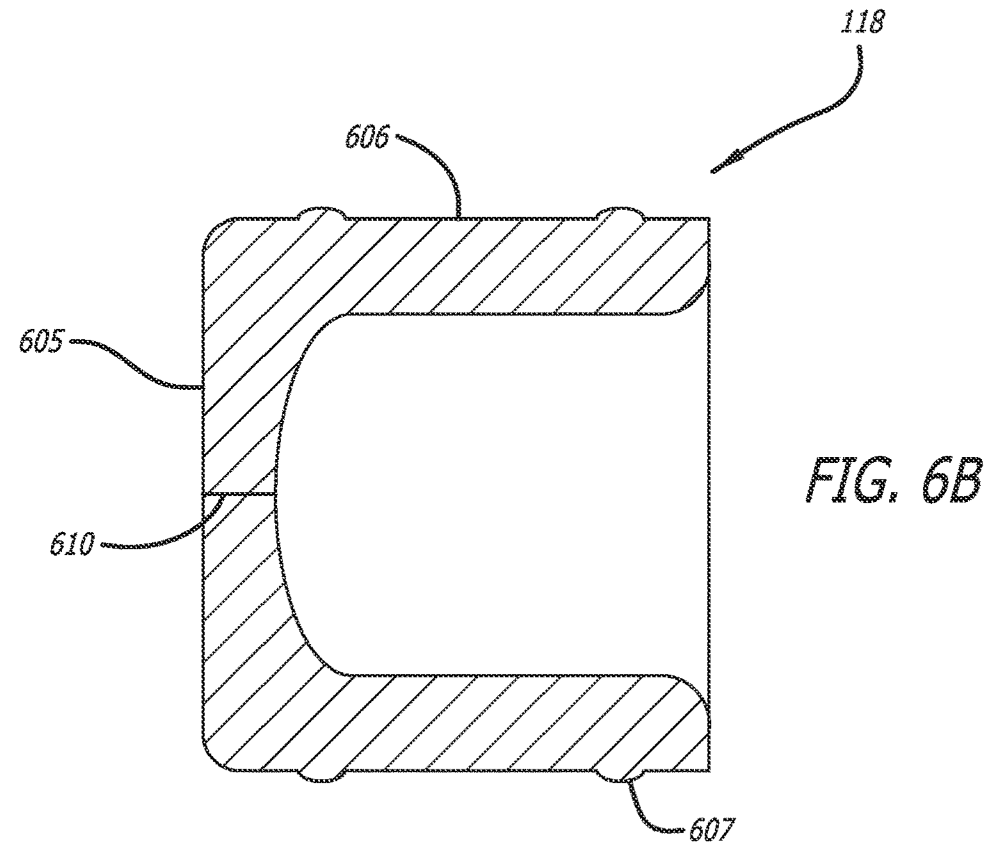
FIG. 6B illustrates a cross-sectional view of the septum of FIG. 6A cut along sectioning lines 6B-6B in accordance with some embodiments.

FIGS. 6A-6B illustrate an exemplary embodiment of the septum 118, where FIG. 6A is a front view of the septum 118 and FIG. 6B is a cross-sectional side view cut along sectioning lines 6B-6B. The septum 118 may take any shape or form consistent with the function of the septum 118. As such, the illustrated form of the septum 118 is just one exemplary form of many which may be contemplated by one of ordinary skill. The septum 118 includes a top wall 605 coupled with a circumferential side wall 606. The side wall 606 is configured to define a fluid tight seal with the hub body 407 when disposed within the needle-hub lumen 550. The side wall 606 may define an interference fit with the needle-hub lumen 550 to secure the septum 118 to the needle hub 106 and to define a fluid tight seal with the hub body 407. In some embodiments, the side wall 606 may include interference elements 607, such as protruding ribs, annular groves, and the like. In some embodiments, the side wall 606 may be adhesively bonded to the needle hub 407. The septum 118 may be formed of any suitable elastomeric material, such as silicone rubber, ethylene propylene diene terpolymer (EPDM), or a polyurethane, for example.

The septum 118 includes a slit 610 extending through the top wall 605. The slit 610 is configured to receive the needle 150 therethrough and provide fluid tight seal with the needle 150. The slit 610 is also configured to sealably close upon withdrawal of the needle 150 to prevent fluid flow across the top wall 605 when the needle 150 is not disposed within the slit 610. In some embodiments, the slit 610 may be formed in the top wall 605 via cutting during the manufacturing process of the septum 118. In other embodiments, the slit 610 may be formed in the top wall 605 by the insertion of the needle 150 during assembly of the central catheter assembly 102.

As an alternative to coupling the septum 118 as separate component to the hub body 407, the septum 118 may be integral to the hub body 407. For example, the hub body 407 and the septum 118 may formed of the same material, and the hub body 407 and the septum 118 may be formed simultaneously via the same process, such as a molding process, for example.

Figures 7, 8A, 8B, 8C, 8D:
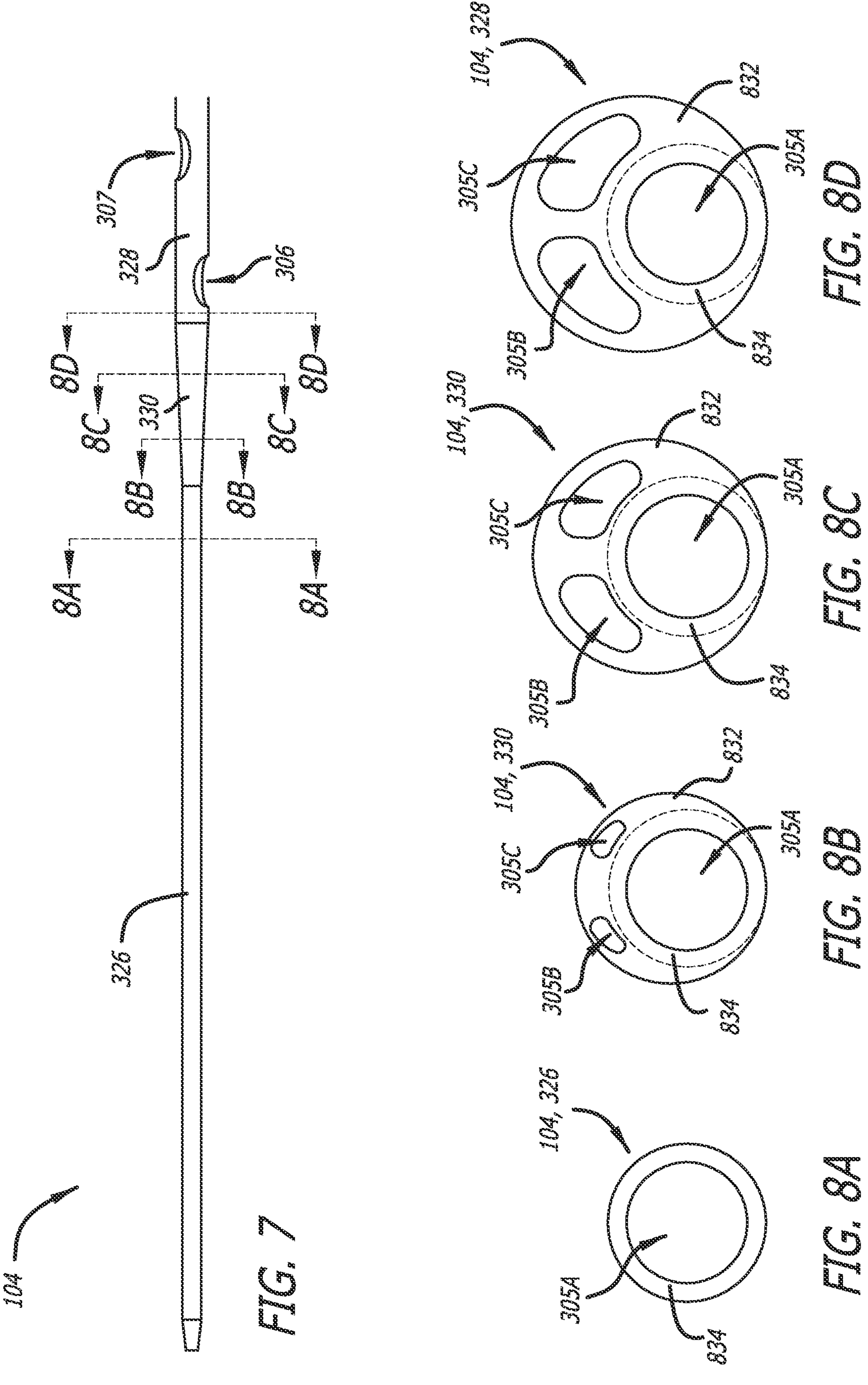
FIG. 7 illustrates a distal portion of the catheter tube of the central catheter of FIG. 3 in accordance with some embodiments.
FIG. 8A illustrates a transverse cross section of a first section of the catheter tube in accordance with some embodiments.
FIG. 8B illustrates a transverse cross section of a transition between the first section and a second section of the catheter tube in accordance with some embodiments.
FIG. 8C illustrates another transverse cross section of the transition between the first section and the second section of the catheter tube in accordance with some embodiments.
FIG. 8D illustrates a transverse cross section of the second section of the catheter tube in accordance with some embodiments.

FIG. 7 further illustrates a distal portion of the catheter tube 104 of the catheter 100 and the components thereof in accordance with some embodiments. FIGS. 8A-8D illustrate various transverse cross sections of the catheter tube 104 in accordance with some embodiments. The first tapered transition portion 330 and the second section 328 of the catheter tube 104 include an outer layer 832 (see FIGS. 8B-8D) of the catheter tube 104 extruded over an inner layer 834 (see FIGS. 8A-8D) of the catheter tube 104 such that an outer diameter of the catheter tube 104 is larger in the second section 328 than the first section 326 of the catheter tube 104 commencing with the first tapered transition portion 330 between the first section 326 and the second section 328 of the catheter tube 104.

The first section 326 of the catheter tube 104 as well as the inner layer 834 of both the first tapered transition portion 330 and the second section 328 of the catheter tube 104 can be formed of a first polymeric material (e.g., polytetrafluoroethylene, polypropylene, or a polyurethane) having a first durometer, while a remainder of the first tapered transition portion 330 and the second section 328 of the catheter tube 104, namely the outer layer 832 thereof, can be formed of a second polymeric material (e.g., polyvinyl chloride, polyethylene, a polyurethane, or silicone) having a second durometer less than the first durometer, more than the first durometer, or substantially equal to the first durometer. For example, each layer of the inner layer 834 and the outer layer 832 of the catheter tube 104 can be made from a different polyurethane (e.g., a same or different diisocyanate or triisocyanate reacted with a different diol or triol, a different diisocyanate or triisocyanate reacted with a same or different diol or triol, etc.) having a different durometer. Polyurethane is advantageous for the catheter tube 104 in that polyurethane can be relatively rigid at room-temperature but become more flexible in vivo at body temperature, which reduces irritation to vessel walls and phlebitis. Polyurethane is also advantageous in that can be less thrombogenic than some other polymers.

Notwithstanding the foregoing, the first tapered transition portion 330 and the second section 328 of the catheter tube 104, which include both the inner layer 834 and the outer layer 832 of the catheter tube 104, can be formed of a same polymeric material (e.g., a polyurethane) with a same durometer provided a column strength of the catheter tube 104 is sufficient to prevent buckling of the catheter tube 104 when inserted into an insertion site and advanced through a vasculature of a patient. The column strength of the catheter tube 104 in any given embodiment is notable in that the column strength makes it possible to rapidly insert the catheter tube 104 into an insertion site and advance the catheter tube 104 through a vasculature of a patient without the using the Seldinger technique.

The catheter tube 104 includes the third section 336 proximal of the second section 328 of catheter tube 104 including an increased diameter demarcated by the second tapered transition portion 331 in the medial portion of the catheter tube 104. The third section 336 of the catheter tube 104 has a larger outer diameter than both the first section 326 and the second section 328 of the catheter tube 104. The needle hub 106 can be disposed over the second tapered transition portion 331 such that the second tapered transition portion 331 including the needle side port 340 is disposed within the hub body 407 (see FIG. 4). Thus, the catheter tube 104 proximal of the needle hub 106 has a larger outer diameter than the catheter tube 104 distal of the needle hub 106. The larger outer diameter of the third section 336 of the catheter tube 104 proximal of the needle hub 106 provides a thicker, more kink-resistant catheter-tube wall useful for bending the manifold hub 108 and the number of extension legs 110 away from a head or neck of a patient while the catheter 100 is in use. In addition, any lumens present in the catheter tube 104 can have a greater diameter in the third section 336 of catheter tube 104 proximal of the needle hub 106 than distal of the needle hub 106. This prevents flow rate reduction, particularly when the third section 336 of the catheter tube 104 proximal of the needle hub 106 is bent away from a head or neck of a patient.

The catheter tube 104 between the needle hub 106 and the manifold hub 108 can include a taper in which the larger outer diameter of the catheter tube 104 continues to increase from the needle hub 106 to the manifold hub 108. In other words, the catheter tube 104 tapers from the manifold hub 108 to the needle hub 106 but continues to have a larger outer diameter than the catheter tube 104 distal of the needle hub 106. In association with the continuously increasing outer diameter of the catheter tube 104 from the needle hub 106 to the manifold hub 108, the catheter-tube wall can continuously increase in thickness, any lumens of the catheter tube 104 can continuously increase in cross-sectional area, or a combination thereof. Consequently, the catheter tube 104 between the needle hub 106 and the manifold hub 108 can be more resistant to kinks and flow rate reduction, particularly when the catheter tube 104 proximal of the needle hub 106 is bent away from a head or neck of a patient. Notwithstanding the foregoing, the catheter tube 104 between the needle hub 106 and the manifold hub 108 can alternatively have a constant diameter from the needle hub 106 to the manifold hub 108.

Advantageously, the catheter tube 104 between the needle hub 106 and the manifold hub 108, namely the third section 336 of the catheter tube 104, is a single catheter tube configured to abate bacterial ingress between a dressing applied over the needle hub 106 and skin of a patient. Existing central venous catheters (CVCs) or peripherally inserted central catheters ("PICCs") have multiple extension legs extending from suture wing-hub combinations common to the CVCs and PICCs. The multiple extension legs in the CVCs or PICCs provide multiple pathways under the dressing for microbial ingress. The catheter tube 104 being a single catheter tube between at least the needle hub 106 and the manifold hub 108 enables the dressing to be pinched more tightly around the catheter tube 104 than possible for the multiple extension legs of the existing CVCs or PICCs. For example, the dressing can be easily wrapped around an entirety of the catheter tube 104 and pinched together under the catheter tube 104 between the catheter tube 104 and the patient. In contrast, even wrapping the dressing around the multiple extension legs of the existing CVCs or PICCs as described for the catheter-tube extension leaves gaps between adjacent extension tubes for bacterial ingress. Thus, the catheter tube 104 being a single catheter tube limits bacterial ingress between the dressing applied over the needle hub 106 and the skin of the patient.

The catheter tube 104 between the needle hub 106 and the manifold hub 108, again the third section 136 of the catheter tube 104 or the catheter-tube extension, is also configured to mitigate patient discomfort from proximity of the number or extension legs 110 to a head or neck of the patient. As set forth above, the third section 336 of the catheter tube 104 proximal of the needle hub 106 provides a thicker, more kink-resistant catheter-tube wall; however, the third section 336 of the catheter tube 104 is flexible enough to enable the catheter tube 104 to be bent away from the head or neck of the patient and secured to the patient for his or her comfort.

Figure 9:
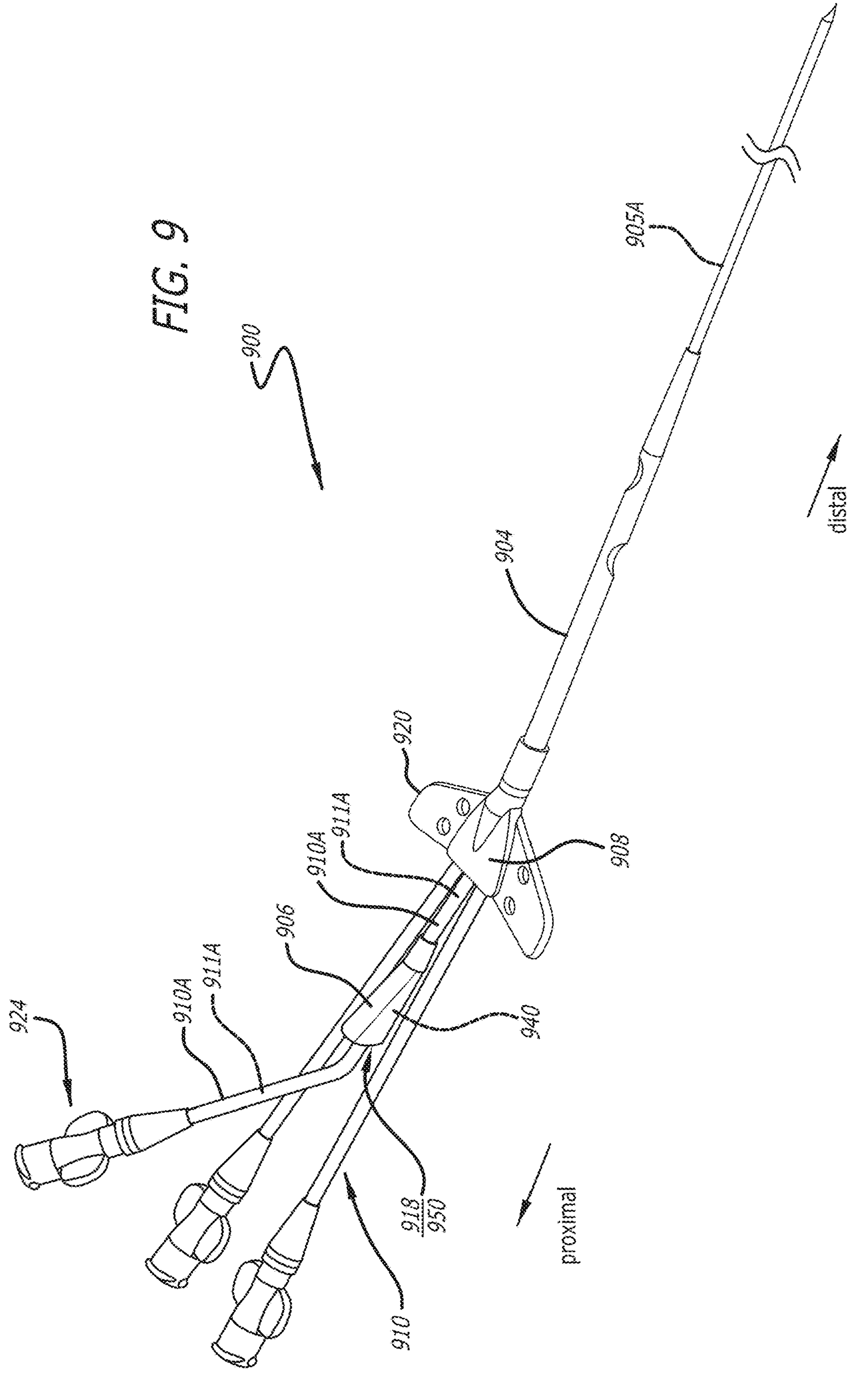
FIG. 9 illustrates another embodiment of a central catheter in accordance with some embodiments.

FIG. 9 illustrates another embodiment of a catheter 900 that can, in certain respects, resemble components of the catheter described in connection with FIGS. 1-8D. It will be appreciated that all the illustrated embodiments may have analogous features. Relevant disclosure set forth above regarding similarly identified features thus may not be repeated hereafter. Moreover, specific features of the catheter and related components shown in FIGS. 1-8D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter of FIG. 9. Any suitable combination of the features, and variations of the same, described with respect to the catheter and components illustrated in FIGS. 1-8D can be employed with the catheter and components of FIG. 9, and vice versa. This pattern of disclosure applies equally to further embodiments depicted in subsequent figures and described hereafter.

The catheter 900 generally includes a catheter tube 904 having a number of catheter-tube lumens extending therethrough and an equal number of the extension legs 910 having Luer connectors 924 disposed their proximal ends. Each catheter-tube lumen is in fluid communication with a corresponding extension-leg lumen. Similar to the catheter 100, the catheter 900 includes a needle hub 906 and a manifold hub 908. The catheter 900 generally differs from the catheter 100 in that the needle hub 906 is disposed proximal the manifold hub 908.

The manifold hub 908 includes the one or more suture wings 920. The needle hub 906 is disposed in line with the primary extension leg 910A. The primary extension leg 910A includes a primary extension-leg lumen 911A that extends from the Luer connector 924 through the needle hub 906 to the manifold hub 908. The needle hub 906 includes a needle hub lumen 950 having a septum 918 disposed therein and the needle hub lumen 950 is configured to receive a needle 150. The primary extension leg 910A includes a needle side port 940 extending through the side wall the primary extension leg 910A. The needle side port 940 is configured to receive the needle therethrough so that the needle 150 may be advanced along the primary extension-leg lumen 911A distal the needle hub 906. Similar to the catheter 100, the catheter 900 may be combined with needle 150 to define a central catheter assembly similar to the central catheter assembly 102 of FIGS. 1-2 where the needle 150 is disposed through the septum 918 into the extension-leg lumen 911A and then advanced along the primary catheter-tube lumen 905A.

Figures 10A, 10B:
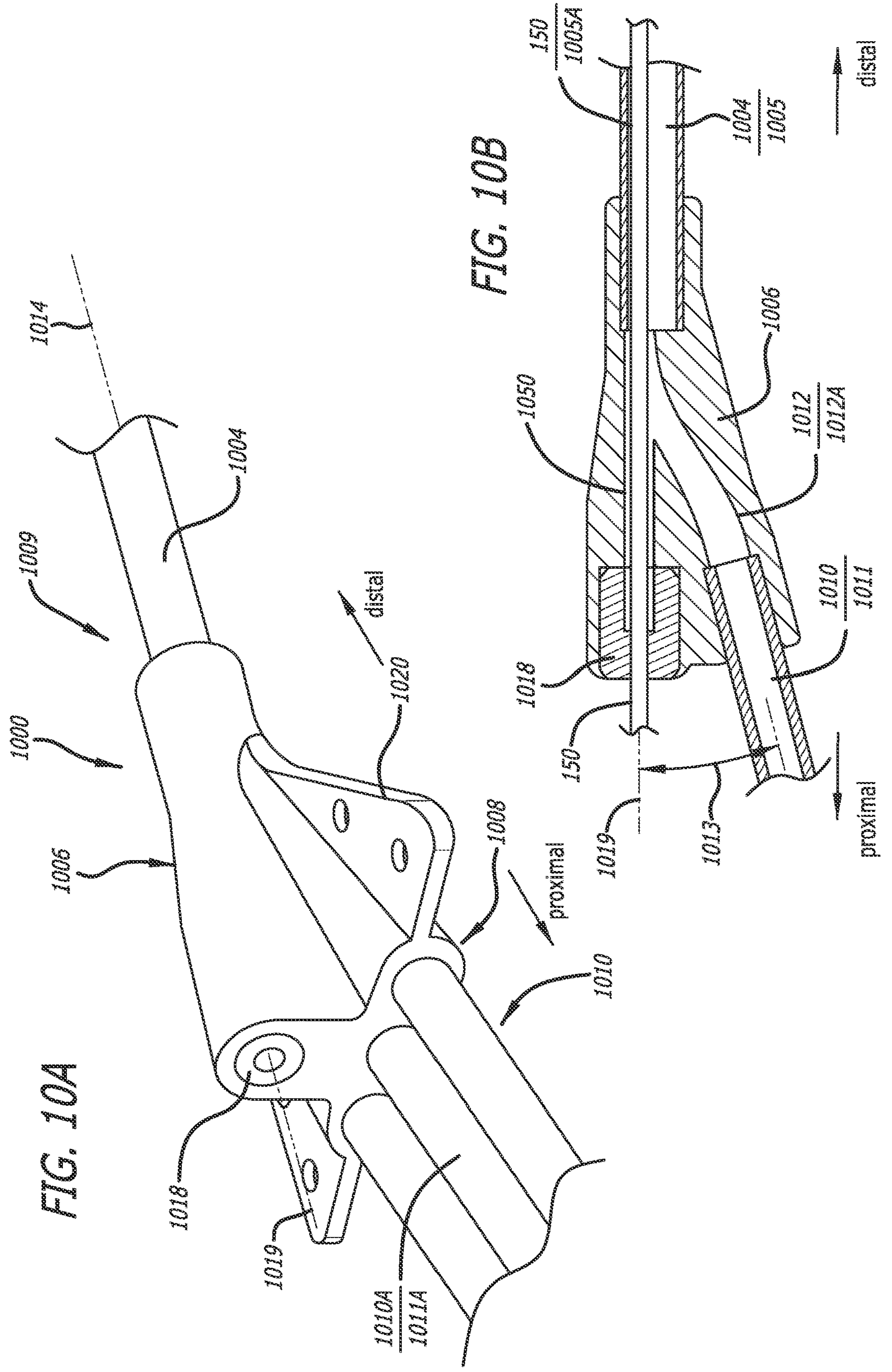
FIG. 10A illustrates a portion of yet another embodiment of a central catheter in accordance with some embodiments.
FIG. 10B illustrates a cross-sectional view of a needle hub of the central catheter of FIG. 10A in accordance with some embodiments.

FIGS. 10A-10B illustrate a portion of a third embodiment of the catheter 1000. Similar to the catheter 900, the catheter 1000 may in certain respects resemble the components and functionality of the catheter 100 described in connection with FIGS. 1-8D. The catheter 1000 includes a combination hub 1006 that incorporates the functionality of the needle hub 106 and the manifold hub 108 of the catheter 100 into a single hub. The catheter 1000 includes a number of extension legs 1010 coupled with the combination hub 1000 at the proximal end 1008 and a catheter tube 1004 coupled with the combination hub 1006 at the distal end 1009. A number of flow lumens 1012 extending through the combination hub 1006 fluidly couple the extension-leg lumens 1011 with the catheter-tube lumens 1005 such that each extension-leg lumen 1011 is in fluid communication with a corresponding catheter-tube lumen 1005. Specifically, the primary extension-leg lumen 1011A of the primary extension leg 1010A is coupled with the primary catheter-tube lumen 1005A via the primary flow lumen 1012A. The needle-hub lumen 1050 is combined with the primary flow lumen 1012A to facilitate passage of the needle 150 through the needle-hub lumen 1050 and further into the primary catheter-tube lumen 1005A. A septum 1018 is disposed with the needle-hub lumen 1050.

The extension legs 1010 extend proximally away from the combination hub 1060 at an angle 1013 with respect to a longitudinal axis 1019 of the needle hub lumen 1050 so that in use, the extension legs 1010 are disposed at an angle with respect to the needle 150 extending proximally away from the combination hub 1006.

One or more suture wings 1020 extend laterally away from the combination hub 1000. In the illustrated embodiment, the suture wings 1020 are disposed parallel with the extension legs 1010. In an alternative embodiment, the suture wings 1020 may be disposed parallel with longitudinal axis 1019 of the needle hub lumen 1050.

The catheter tube 1004 extends distally away from the combination hub 1006 a longitudinal axis 1014 and in some embodiments, the longitudinal axis 1019 of the needle hub lumen 1050 and the longitudinal axis 1014 are parallel with each other. In further embodiments, the primary catheter-tube lumen 1005A may define the longitudinal axis 1014 and the longitudinal axis 1014 may be colinear with the longitudinal axis 1019.

Figure 11:
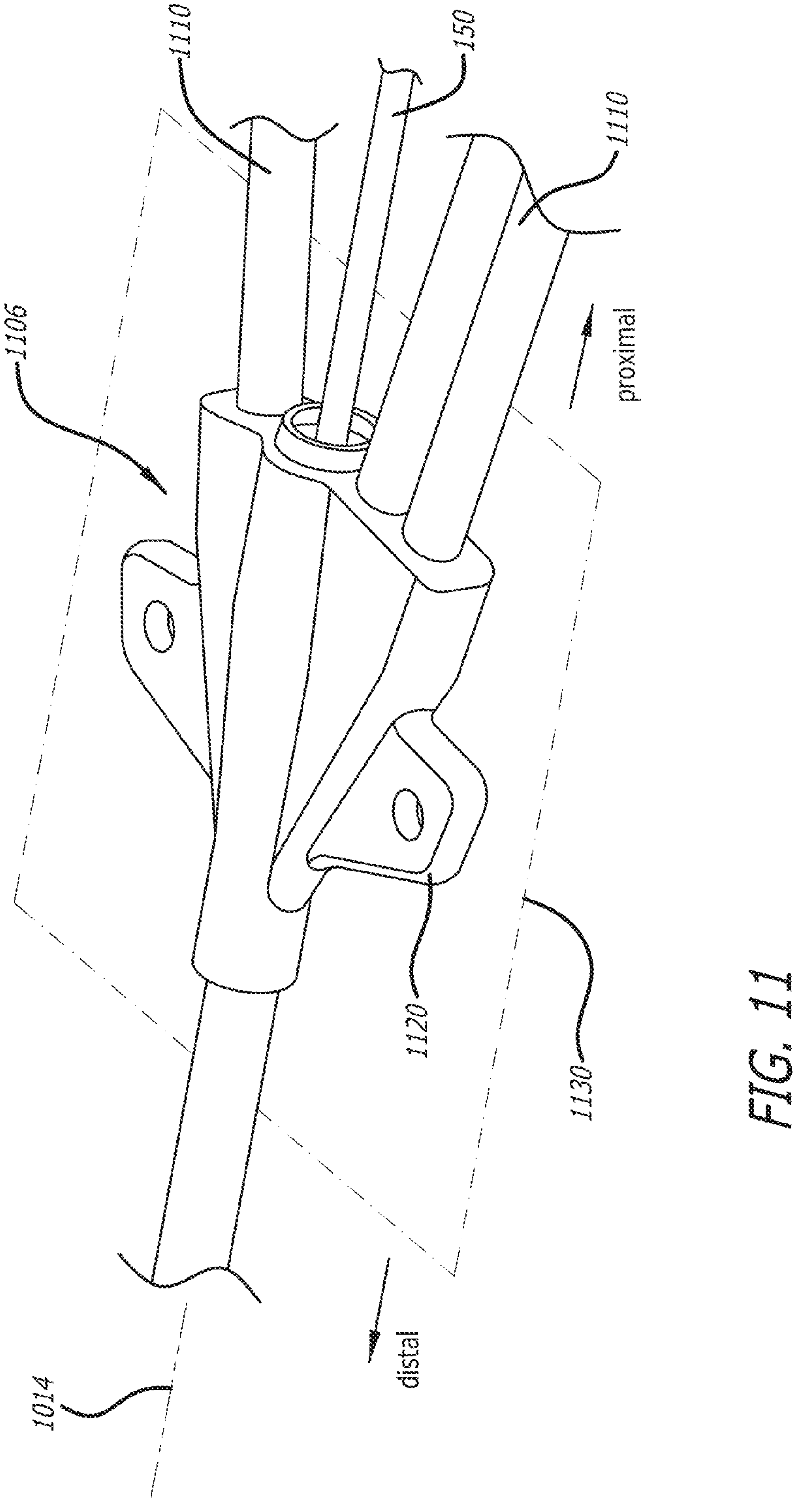
FIG. 11 illustrates another embodiment of the needle hub of FIGS. 10A-10B in accordance with some embodiments.

FIG. 11 illustrates a second embodiment of the combination hub. The combination hub 1106 may in certain respects resemble the components and functionality of the combination hub 1006. The combination hub 1106 generally includes a flat shape defining a plane 1130. As such, the extension legs 1110 and the needle 150, when the needle is disposed in the needle hub lumen, extend proximally away from the combination hub 1106 within the plane 1130 i.e., portion of the extension legs 1110 the needle 150 adjacent the combination hub 1106 are disposed within the plane 1130. Similarly, the catheter tube 1104 extends distally away from the combination hub 1106 within the plane 1130. The suture wings 1120 may also be disposed within or extend along the plane 1130. To provide access to the needle 150 (i.e., grasping of the needle 150), the extension legs 1110 extend proximally away from the combination hub 1106 at an angle with respect to the needle 150 when present.

A method for introducing a central catheter into a blood vessel of a patient may include providing a central catheter that includes a catheter tube having a catheter-tube lumen extending therethrough to a distal end of the catheter tube and a needle hub coupled with the catheter tube. The needle hub includes a needle-hub lumen configured for advancement of a needle therethrough and a septum disposed across a proximal portion of the needle-hub lumen, where the septum is configured to (i) define a fluid tight seal with the needle when the needle is disposed within the needle-hub lumen and (ii) prevent fluid flow through the proximal portion of the needle-hub lumen when the needle is not disposed within the needle-hub lumen. The needle hub is coupled with the catheter tube such that the needle-hub lumen is in fluid communication with the catheter-tube lumen.

The method further includes inserting the catheter tube through a skin of the patient to the blood vessel such that the distal end of the catheter is disposed within the blood vessel, where the catheter-tube lumen includes a needle disposed therein. The method may further include advancing the catheter tube along the needle to advance the catheter tube further into the blood vessel lumen. The method may further include withdrawing the needle from the catheter-tube lumen.

In some embodiments, the method may include inserting the needle through the needle-hub lumen into the catheter-tube lumen.

In some embodiments, the method may include aspirating blood from the blood vessel with a syringe connected to the needle before withdrawing the needle from the catheter-tube lumen. Aspirating the blood may confirm that the distal tip of the needle is disposed within the blood-vessel lumen.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A central catheter, comprising:
- a catheter tube configured for advancement along a vasculature of a patient, the catheter tube including a number of catheter-tube lumens extending along the catheter tube, wherein the catheter tube defines a first section having a first diameter, a second section proximal the first section having a second diameter greater than the first diameter, and a third section proximal the second section and having a third diameter greater than the second diameter, and wherein the catheter tube further defines a first tapered portion between the first section and the second section and a second tapered portion between the second section and the third section;
- a needle side port disposed on the second tapered portion, the needle side port extending through a side wall of the catheter tube in fluid communication with one of the number of catheter-tube lumens;
- a number of extension legs equal to the number of catheter-tube lumens, wherein each extension leg of the number of extension legs is in fluid communication with a corresponding catheter-tube lumen of the number of catheter-tube lumens; and
- a needle hub coupled with the catheter tube, including:
  - a needle-hub lumen configured for advancement of a needle therethrough, wherein the needle-hub lumen is parallel with the catheter tube along a distal portion of the needle hub; and
  - a septum disposed across a proximal portion of the needle-hub lumen, the septum configured to:
    - define a fluid tight seal with the needle when the needle is disposed within the needle-hub lumen, and
    - prevent fluid flow through the proximal portion of the needle-hub lumen when the needle is not disposed within the needle-hub lumen; and
- wherein the needle hub is coupled with the catheter tube such that the needle-hub lumen is in fluid communication with one of the number of catheter-tube lumens through the needle side port.

2. The catheter according to claim 1, wherein the needle-hub lumen is colinear with one of the number of catheter-tube lumens along the distal portion of the needle hub.

3. The catheter according to claim 1, wherein the needle hub further includes one or more suture wings for securing the needle hub to the patient.

4. The catheter according to claim 3, wherein:
- the one or more suture wings define a patient contact surface of the needle hub, and
- the patient contact surface is parallel with the needle-hub lumen.

5. The catheter according to claim 1, further comprising a manifold hub defining the fluid communication between each extension leg of the number of extension legs and the corresponding catheter-tube lumen.

6. The catheter according to claim 5, wherein the number of extension legs are attached to the manifold hub.

7. The catheter according to claim 5, further comprising a combination hub including the needle hub and the manifold hub, wherein the number of extension legs are attached to the combination hub.

8. The catheter according to claim 7, wherein each extension leg of the number of extension legs is attached to the combination hub at an angle with respect to the needle-hub lumen.

9. The catheter according to claim 7, wherein each extension leg of the number of extension legs is attached to the combination hub at an angle with respect to a patient contact surface.

10. The catheter according to claim 7, wherein the number of extension legs are attached to the combination hub within a plane.

11. The catheter according to claim 1, wherein each extension leg of the number of extension legs includes a Luer connector at a proximal end thereof.

12. The catheter according to claim 1, wherein the number of catheter-tube lumens includes:

a primary lumen extending distally to a distal end of the catheter tube;

a secondary lumen extending distally to a first side port of the catheter tube, the first side port disposed proximal the distal end of the catheter tube; and a tertiary lumen extending distally to a second side port of the catheter tube, the second side port disposed proximal the first side port.

13. The catheter according to claim 1, wherein a material of the septum is one of a silicone rubber, an ethylene propylene diene terpolymer, or a polyurethane.

14. The catheter according to claim 1, wherein the needle hub and the septum are composed of a same material.

15. The catheter according to claim 1, wherein the septum is formed integral to the needle hub during a forming process of the needle hub.

16. The catheter according to claim 1, wherein the septum includes a preformed slit configured for insertion of the needle therethrough.

17. A central catheter assembly, comprising:

the central catheter according to claim 1; and the needle preloaded in the central catheter, the needle disposed within the needle-hub lumen and within a primary catheter-tube lumen of the number of catheter-tube lumens.

18. The assembly according to claim 17, wherein a distal tip of the needle extends beyond a distal end of the catheter tube to facilitate a percutaneous puncture with the needle.

19. The assembly according to claim 17, wherein the needle includes a lubricant disposed on an outside surface of the needle to facilitate a sliding engagement of the needle with the septum.

20. The assembly according to claim 17, wherein the number of extension legs includes a primary extension leg in fluid communication with the primary catheter-tube lumen, the assembly further including a preloaded guidewire disposed within the primary extension leg.

* * * * *